US00PP24108P3

(12) United States Plant Patent
Hurd

(10) Patent No.: US PP24,108 P3
(45) Date of Patent: Dec. 24, 2013

(54) ***HIBISCUS* PLANT NAMED 'MY VALENTINE'**

(50) Latin Name: ***Hibiscus* hybrid (L.)**
Varietal Denomination: My Valentine

(75) Inventor: Kevin A. Hurd, Chicago, IL (US)

(73) Assignee: Walters Gardens Inc, Zeeland, MI (US)

( * ) Notice: Subject to any disclaimer, the term of this patent is extended or adjusted under 35 U.S.C. 154(b) by 92 days.

(21) Appl. No.: 13/385,986

(22) Filed: Mar. 19, 2012

(65) Prior Publication Data

US 2013/0247258 P1 Sep. 19, 2013

(51) Int. Cl.
*A01H 5/00* (2006.01)

(52) U.S. Cl.
USPC ..... Plt./257

(58) Field of Classification Search
USPC ..... Plt./257
See application file for complete search history.

*Primary Examiner* — Susan McCormick Ewoldt

(57) ABSTRACT

A new and distinct cultivar of hardy herbaceous *Hibiscus* hybrid plant named 'My Valentine' is winter-hardy with naturally short, mounded habit with dense heavy branching. The foliage is fine textured tri-lobed and of dark green with purple tinting and veining. The flowers are large and numerous with red-velvet overlapping, slightly-recurved petals over a long blooming period.

1 Drawing Sheet

Botanical classification: *Hibiscus* hybrid (L.)
Variety denomination: 'My Valentine'.

BACKGROUND AND ORIGIN OF THE PLANT

The present invention relates to the new and distinct hardy, herbaceous, *hibiscus* plant, *Hibiscus* 'My Valentine' hybridized by Kevin A. Hurd in the summer of 2007 at a nursery in Zeeland, Mich. The new plant, originally labeled #07-57-07, is from a cross between the proprietary hybrid #04-17-13 (not patented) (female pod parent) times the proprietary hybrid # 05-255-08 (not patented) (male pollen parent). Both parents have a complex mixture of species in them, most likely including the species: *moscheutos, coccineus* and *laevis*. *Hibiscus* 'My Valentine' was first asexually propagated in 2009 by both stem cuttings and sterile tissue culture at the same nursery in Zeeland, Mich. The resultant plants have been found to be stable and true to type in successive generations of asexual reproduction.

BRIEF SUMMARY OF THE PLANT

*Hibiscus* 'My Valentine' differs from its parents as well as all other hardy *hibiscus* known to the applicant in many traits. The foliage color of 'My Valentine' is a dark green with burgundy tinting and veining. The foliage shape of 'My Valentine' is heterophyllous, depending on the time of year and position on the stem and rate of growth. Upper leaves on rapidly growing stems may be nearly lanceolate to ovate with rounded base and narrowly acute apex. Lower leaves on more mature plants may be palmately tri-lobed to five-lobed. The flower of 'My Valentine' is comprised of slightly-recurved red-velvet petals with columns of complimenting light yellow pollen.

The cultivars most similar to *Hibiscus* 'My Valentine' are *Hibiscus* 'Fireball' U.S. Plant Pat. No. 13,631, *Hibiscus* 'Lord Baltimore' (not patented), *Hibiscus* 'Robert Fleming' U.S. Plant Pat. No. 14,776 and *Hibiscus* 'Sultry Kiss' U.S. Plant Pat. No. 22,300. The new plant is taller than 'Robert Fleming', with lighter red flower and foliage that is flatter, less rugose and darker green. Compared to 'Fireball', 'My Valentine' has more compact shorter habit with less sprawling and angled stems, the foliage is less cleft or dissected, not as wide and the flower of 'Fireball' has a more blue tint and less bright red. 'My Valentine' is shorter and more branched than 'Lord Baltimore' and has more fertile flowers with petals that overlap more. Compared to 'Sultry Kiss' the new plant has darker red flowers and darker leaves.

In comparison to the parents, 'My Valentine' is shorter, more compact in habit and with slightly smaller thicker-substance flowers than #04-17-13. In comparison to #05-255-08 the new plant has a deeper red flower, longer bloom time and more dissected foliage.

*Hibiscus* 'My Valentine' is a unique hardy herbaceous *hibiscus* with the following combined traits:

1. Winter-hardy, naturally short, mounded habit with dense heavy branching.
2. Many flowers with red-velvet, overlapping, slightly-recurved petals.
3. Fine textured foliage of dark green with purple tinting and veining.

BRIEF DESCRIPTION OF THE DRAWINGS

The photograph of the new plant demonstrates the overall appearance of the plant, including the unique traits. The colors are as accurate as reasonably possible with color reproductions. Ambient light spectrum, source and direction may cause the appearance of minor variation in color. The plant in the photograph is a two-year old plant growing in a full-sun field loamy-sand soil environment with supplemental water and fertilizer as required.

FIG. 1 shows the new plant in full flower with variable foliage shapes, flowers and buds.

DETAILED BOTANICAL DESCRIPTION

The following descriptions and color references are based on the 2001 edition of The Royal Horticultural Society Colour Chart except where common dictionary terms are used. The new plant, *Hibiscus* 'My Valentine', has not been observed under all possible environments. The phenotype may vary slightly with different environmental conditions, such as temperature, light, fertility, moisture and maturity levels, but without any change in the genotype. The following observations and size descriptions are of two-year old plants in the loamy-sand open field trials of a nursery in Zeeland, Mich. with supplemental fertilizer and water as needed. The plants are natural habit and were not treated with plant growth regulators, nor were they pinched at any time in the growth year.

Parentage: Proprietary hybrid # 04-17-13 (not patented) (female pod parent) times the proprietary hybrid # 05-255-08 (not patented) (male pollen parent).

Propagation:

*Method*.—Stem cuttings and sterile plant tissue culture division.

*Time to initiate roots from tissue culture*.—About two weeks.

*Rooting habit*.—Normal, branching, developing thick to about 4 cm diameter, fleshy; root color creamy white between RHS 159A and lighter than RHS 159 D depending on soil type.

*Crop time*.—Under normal summer growing conditions 12 to 16 weeks to flower in a four-liter container from cutting. Plant vigor is very good.

Plant description:

*Plant shape and habit*.—Winter-hardy, multi-stemmed, herbaceous perennial with 10 to 18 thick upright and heavily branched main stems producing a rounded mound; 9 to 12 primary branches per main stem protruding at 45° to 75° angle from horizontal, secondary branches on the lower two thirds to one half of the primary branches; primary branch size: between 8.0 cm and 40.0 cm long (shorter at the upper nodes) and 0.4 cm to 1.0 cm diameter at the base of branch; secondary branches to 4.5 cm long and 3.0 mm wide at base.

*Plant size*.—Unpinched plant with stems 90 to 120 cm tall, average about 115 cm tall from soil line, and diameter at base average about 2.8 cm; overall plant 80 to 95 cm wide about 30 cm above the base (widest point), average about 88 cm.

*Internode length*.—Unpinched plant varied between 2.0 to 5.0 cm, average about 4.0 cm.

*Foliage description*.—Alternate; dentate; glabrous; heterophyllous; base equilateral, rounded base, acute apex; palmatifid, mostly deeply and sharply cleft trilobed with openings than 45 degrees; some immature leaves oblong ovate with ovate bases and acute apexes, texture dull above and below with younger developing leaves lustrous; palmately veined; leaf size 11.0 cm to 15.0 cm long and 9.0 to 11.0 cm wide, becoming smaller in distal portion of stem.

*Foliage color*.—Adaxial side between RHS 139A and RHS 139B with greyed-purple tinting of between RHS N187A and RHS N186C; abaxial side between RHS 139C and RHS 139D.

*Veins*.—Reticulate; primary adaxial veins variable in color; lower leaves with mostly between RHS 144B and RHS 144C with some tinting in the center of the leaves becoming purplish nearest RHS 185B in the lower center main vein while veins in the upper leaves with deeper purple nearest RHS 187D and fewer green veins of nearest RHS 144B; main abaxial veins of lower leaves RHS 187C with secondary veins nearest RHS 144B, main abaxial veins upper leaves between RHS 187C and RHS 187B, secondary veins between RHS 144C and RHS 143C.

*Petioles*.—Average size 5.0 cm long and 3.0 mm wide; mostly cylindrical with proximal petioles more plano-convex; color above nearest to RHS 185C or in more light nearest RHS 185A, below between RHS 185D and RHS 185C; last distal centimeter before leaf blade between RHS 138A and RHS 144A.

Flower description:

*Buds*.—One day prior to opening about 7.0 cm long and 3.0 cm in diameter, acute apex and bluntly rounded base, unopened petals wrinkled at veins, exposed petal color nearest RHS 187B; prior to showing petals buds are about 3.3 cm long and 2.5 cm in diameter, ovoid with acute apex, carinate at the fusion seam of the sepals; color between RHS 138A and RHS 138B with tinting and sepal carina between RHS N186C and RHS 183A.

*Epicalyx*.—Entire, smooth, glabrous, linear with sharply acute apex, curved around sepals; 10 to 12 per flower; 2.6 cm long tapering to base of 3.0 mm wide; adaxial color RHS 144A, abaxial color RHS 144C, with occasional tinting of apex nearest RHS N186C.

*Sepals*.—5, glabrous, proximal half connate forming campanulate star-shaped calyx; acute apex; margin entire, edentate; about 4.0 cm long and 2.5 cm wide; abaxial color nearest RHS 144A and adaxial color between RHS 144C and RHS 143D; five primary sepal veins nearly same color as sepal, between RHS 144C and RHS 144D on inside and nearest RHS 144A on outside.

*Flowers*.—Solitary, 15 to 18 per main stem without pinching; petals slightly recurved producing a flat face with concaved center eye; upward and outwardly facing to display whole face; average 21.0 cm across and 8.5 cm deep, larger in early part of flowering season; persist for one to two days; effective for at least 12 weeks beginning mid-July and lasting into October; no detectable fragrance.

*Petals*.—Five; glabrous, dull in the outer two thirds and shiny in the inner one third, adnate to the androecium, imbricate to about 100% overlapping at widest part (petals completely overlapping to the edge of the next petal in the position two over); shape rounded; margins entire; apex rounded; base short claw-like; veins slightly impressed, surface otherwise flat, without intense ruffles; about 12.0 cm long and 12.0 cm wide at widest portion (larger in earlier part of flowering season and smaller later in flowering season).

*Petal color*.—Adaxial surface between RHS 46B and RHS 53B on distal three quarters; shiny and nearest RHS 53A at base one quarter lightening to between RHS 45C and RHS 46C just before column attachment; abaxial surface between RHS 59B and RHS 60A except for the basal 2.0 cm which is between RHS 53C and RHS 53B.

*Petal veins*.—Diadromous; about 18 to 20 veins; slightly impressed on adaxial surface and heavily ribbed on the abaxial surface.

*Petal vein color*.—Adaxial surface center nearest RHS 53B and blending with petal color distally and petal eye proximally; abaxial shiny and between RHS 46A and RHS 46B.

*Gynoecium*.—Pistil: mostly enclosed in column that is about 6.5 cm long and 1.0 cm wide at base; Column color: striated length-wise at the basal 2.0 cm with darkest portions nearest RHS 63A extending up the column from center of petals and lightest portion nearest RHS 56D extending up the column from edge of petals; distal 4.5 cm of column nearest RHS 61C; Style: distal 1.0 cm portion of style split into five branches and protrudes from column, branch diameter 2.0 mm, branch color nearest RHS 59C; Stigma: five; globose, puberulose, about 3 mm in diameter, nearest RHS 59A; Ovary: nearest RHS 145C.

*Androecium*.—Filaments: numerous, about 120; about 6.0 mm long and 0.5 mm in diameter; attached to nearly the entire length of column; nearest RHS 53C; Anthers: reniform; dorsifixed; longitudinal; about 2 mm long and 1 mm wide; between RHS 53C and RHS 53D; Pollen: numerous, globose, less than 0.1 mm long, between RHS 19D and RHS 158D.

Pedicel: From base of sepal to abscission point average 1.5 cm long and 4 mm wide on early flowers decreasing in distal flowers; color nearest RHS 184C with high light exposure and nearest RHS 138B with more shading.

Peduncle: Flowers are easily visible, held out on average 5.5 cm long from abscission point to stem and 4 mm wide on early flowers shortening to about 5.0 cm distally on stem; distal 1.0 cm nearest RHS 138B and lower color between RHS 183B and RHS 184C with light exposure and nearest 138B with more shading and at base nearest stem.

Fruit: Loculicidal capsule; glabrous; globose, occasionally with abruptly acute apex; RHS N199B when mature.

Seed: Spherical, minutely floccose, globose to slightly reniform; 3 to 4 mm in diameter; RHS 200A.

Disease resistance: Resistance beyond that of other hardy *hibiscus* cultivars has not been observed. The plant grows best with plenty of moisture and adequate drainage, but is able to tolerate some drought when mature. Hardiness at least from USDA zone 4 through 9, and other disease resistance is typical of that of other *hibiscus* cultivars.

I claim:

1. A new cultivar of hardy herbaceous *Hibiscus* hybrid plant named 'My Valentine' as herein illustrated and described and photographed, comprising winter-hardy, naturally short, mounded habit with dense heavy branching; with fine textured tri-lobed foliage of dark green with purple tinting and veining and many red-velvet flowers having overlapping, slightly-recurved petals over a long blooming period; suitable for potted plant culture and landscaping as a specimen, small group or en masse.

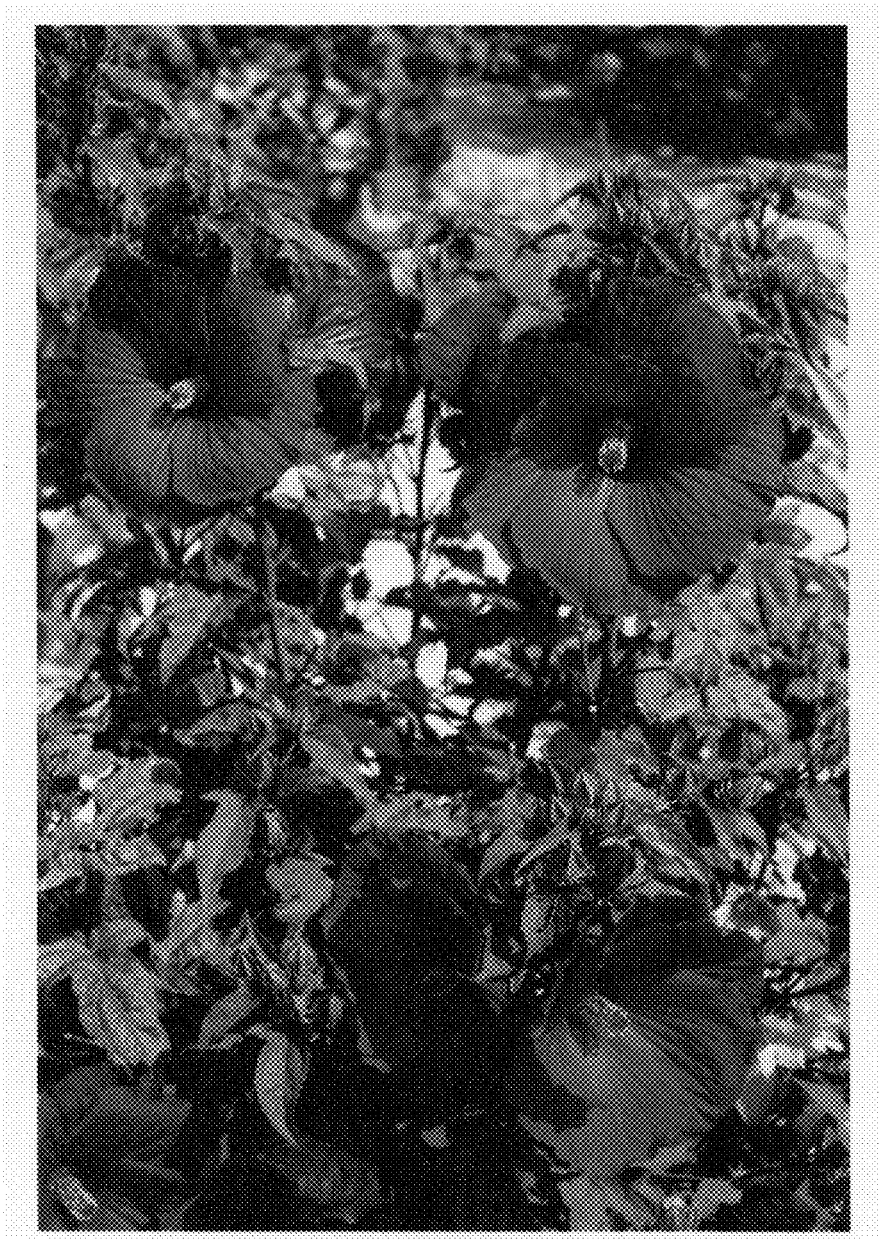

* * * * *